United States Patent [19]
Fukuda et al.

[11] Patent Number: 6,066,742
[45] Date of Patent: May 23, 2000

[54] INTERMEDIATES FOR THE PREPARATION OF DUOCARMYCIN SA AND DERIVATIVES THEREOF, AND PROCESS FOR THE PRODUCTION OF THE INTERMEDIATES

[75] Inventors: Yasumichi Fukuda, Tochigi; Shiro Terashima, Tokyo, both of Japan

[73] Assignees: Kyorin Pharmaceutical Co., Ltd., Tokyo; Sagami Chemical Research Center, Kanagawa, both of Japan

[21] Appl. No.: 09/254,515

[22] PCT Filed: Jun. 26, 1997

[86] PCT No.: PCT/JP97/02207

§ 371 Date: Mar. 9, 1999

§ 102(e) Date: Mar. 9, 1999

[87] PCT Pub. No.: WO98/12197

PCT Pub. Date: Mar. 26, 1998

[30] Foreign Application Priority Data

Sep. 18, 1996 [JP] Japan ................................. 8-246097

[51] Int. Cl.[7] ...................... C07D 487/04; C07D 209/12
[52] U.S. Cl. ............................. 548/433; 548/500
[58] Field of Search ...................... 548/433, 580

[56] References Cited

PUBLICATIONS

Boger et al., J. Am. Chem. Soc., 1993, vol. 115, pp. 9025–9036.
Fukuda et al., Tetrahedron, 1994, vol. 50, No. 9, pp. 2793–2808.
Boger et al., J. Am. Chem. Soc., May 28, 1997, vol. 119, pp. 4977–4986.

*Primary Examiner*—Laura L. Stockton
*Attorney, Agent, or Firm*—McAulay Nissen Goldberg & Kiel, LLP

[57] ABSTRACT

Indole derivatives shown by the formulae (1), (2a) and (2b)

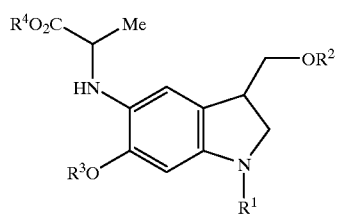

(1)

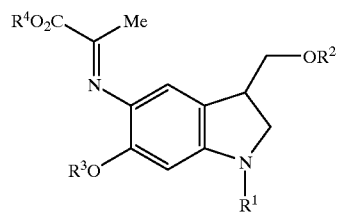

(2a)

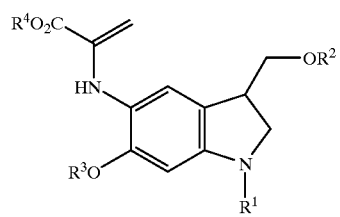

(2b)

(wherein $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group), and pyrroloindole derivatives shown by formula (3)

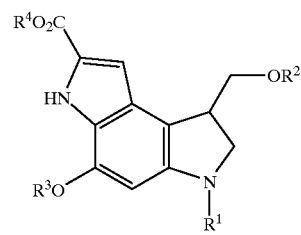

(3)

(wherein $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group), both of which are intermediates for duocarmycin SA, which is expected to be used as an anticancer agent, and derivatives thereof; and a method for producing the same.

5 Claims, No Drawings

INTERMEDIATES FOR THE PREPARATION OF DUOCARMYCIN SA AND DERIVATIVES THEREOF, AND PROCESS FOR THE PRODUCTION OF THE INTERMEDIATES

This application is a 371 of PCT/JP97/02207 filed Jun. 26, 1997.

TECHNICAL FIELD

The present invention relates to intermediates of duocarmycin SA and its derivatives, and methods for producing the same. Duocarmycin SA is a pyrroloindole derivative shown by the formula A and expected to be used as an anticancer agent.

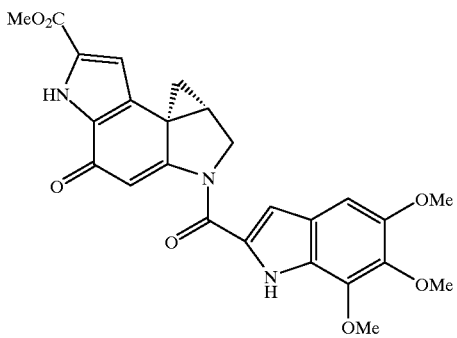

A

BACKGROUND ART

Intermediates of duocarmycin SA, which is expected to be used as an anticancer agent, and derivatives thereof, and production of these compounds have been disclosed, for example, in J. Antibiotics 43, 1037 (1990), ibid. 44, 1045 (1991), Japanese Patent Laid-open Pub. No. Hei 2-177890, Japanese Patent Laid-open Pub. No. Hei 5-208979, Japanese Patent Laid-open Pub. No. Hei 7-53558, J. Am. Chem. Soc. 114, 10056 (1992), Tetrahedron Lett. 35, 2573 (1994), and Chem. Pharm. Bull. 43, 1064 (1995).

Among these known methods for producing duocarmycin SA and its derivatives, the method by formentation allows only a low productivity, and the chemical synthesis needs many steps for producing an optically active one or accompanies arduous optical resolution of an intermediate. Thus, it was difficult to efficiently produce optically active duocarmycin SA.

The object of the present invention is to provide intermediates for efficiently producing duocarmycin SA, which is expected to be used as an anticancer agent, and its derivatives, and methods for producing the same.

DISCLOSURE OF THE INVENTION

The inventors provide indole derivatives and pyrroloindole derivatives both of which are intermediates for duocarmycin SA and derivatives thereof, shown by the formula (1)

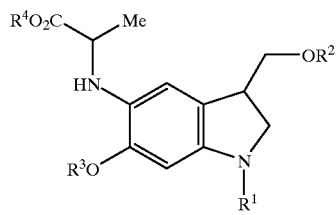

(1)

wherein, $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group, the formula (2a) or (2b)

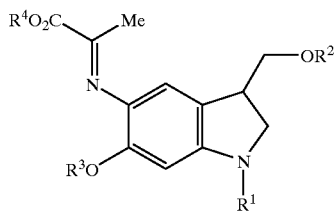

(2a)

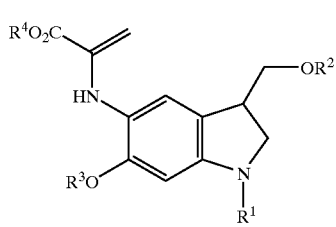

(2b)

wherein, $R^1$, $R^2$, $R^3$, and $R^4$ are the same as described above, and the formula (3)

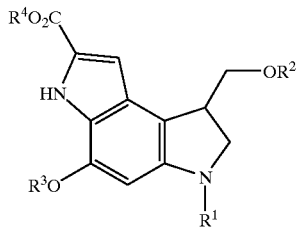

(3)

wherein, $R^1$, $R^2$, $R^3$, and $R^4$ are the same as described above.

The inventors also provide a method for producing a pyrroloindole derivative, which is an intermediate of duocarmycin SA and its derivatives, shown by the formula (3),

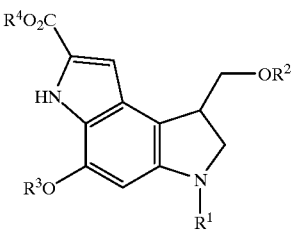

(3)

comprising oxidative cyclization of an indole derivative shown by the formula (1),

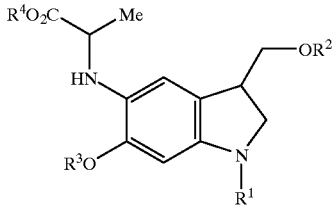
(1)

as well as a method for producing a pyrroloindole derivative, which is an intermediate of duocarmycin SA and its derivative, shown by the formula (3),

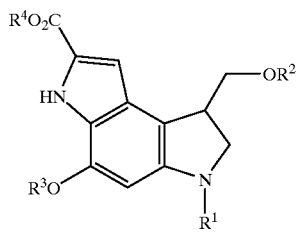
(3)

comprising oxidative cyclization of an indole derivative shown by the formula (2A) or (2b).

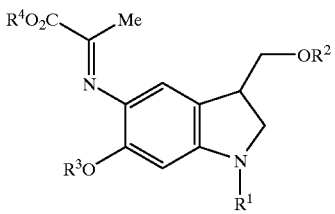
(2a)

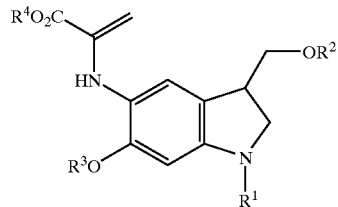
(2b)

$R^1$, which is a protecting group for amino group, includes a $C_1$–$C_6$ linear or branched lower alkoxycarbonyl such as methoxycarbonyl, ethoxycarbonyl, isopropoxycarbonyl, and t-butoxycarbonyl; a haloalkoxycarbonyl such as 2,2,2-trichloroethoxycarbonyl and 2,2,2-trichloro-1,1-dimethylethoxycarbonyl; and a substituted or unsubstituted aralkyloxycarbonyl such as benzyloxycarbonyl, 4-methylbenzyloxycarbonyl, 3-chlorobenzyloxycarbonyl, 4-methoxybenzyloxycarbonyl, benzhydrylcarbonyl, di-(4-methoxyphenyl)methoxycarbonyl, trityloxycarbonyl, and fluorenylmethoxycarbonyl.

$R^2$, which is a protecting group for hydroxyl group, includes a $C_1$–$C_6$ linear or branched substituted or unsubstituted lower alkanoyl such as formyl, acetyl, methoxyacetyl, phenoxyacetyl, and pivaloyl; a substituted or unsubstituted aryloyl such as benzoyl, toluoyl, 3-chlorobenzoyl, and 4-phenylbenzoyl; a substituted or unsubstituted arylmethyl such as benzyl, 4-methylbenzyl, 3-chlorobenzyl, 4-methoxybenzyl, 2,4-dimethoxybenzyl, benzhydryl, di-(4-methoxyphenyl)methyl, and trityl; and a substituted silyl such as triethylsilyl, isopropyldimethylsilyl, t-butyldimethylsilyl, and t-butyldiphenylsilyl.

$R^3$, which is a protecting group for hydroxyl group, includes a $C_1$–$C_6$ linear or branched lower alkyl such as methyl and ethyl; and a substituted or unsubstituted arylmethyl such as benzyl, 4-methylbenzyl, 3-chlorobenzyl, 4-methoxybenzyl, 2,4-dimethoxybenzyl, benzhydryl, di-(4-methoxyphenyl)methyl, and trityl.

$R^4$ includes a $C_1$–$C_6$ linear or branched lower alkyl such as methyl, ethyl, propyl, butyl, isopropyl, and t-butyl.

The compounds according to the present invention can be produced following to the steps shown below:

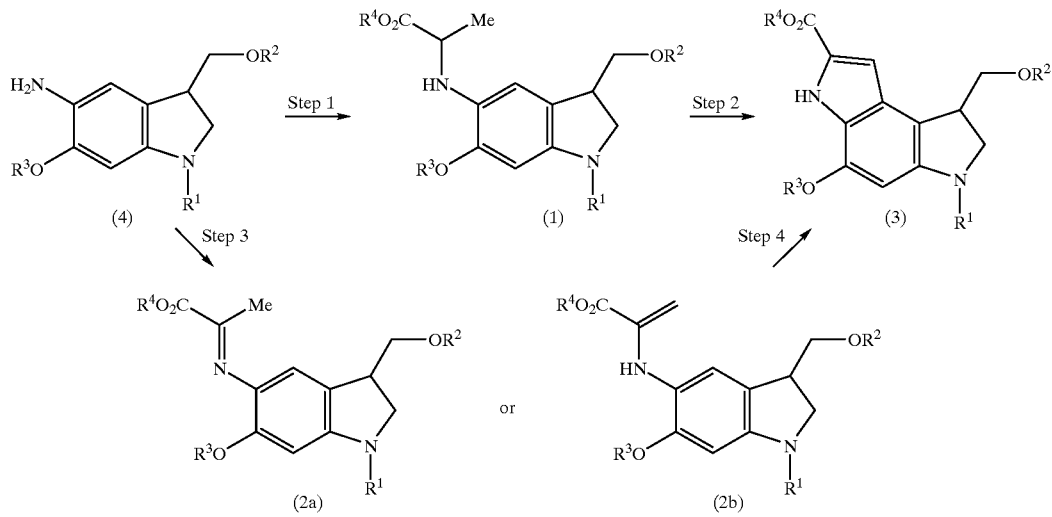

Step 1

This step is a step to produce a compound shown by the formula (1) from a compound shown by the formula (4). The step can be performed by well-known methods, for example, according to Tetrahedron 50, 2793 (1994).

Step 2

This step is a step to produce a compound shown by the formula (3) by oxidative cyclization of a compound shown by the formula (1). The oxidative cyclization according to the present invention is performed using a palladium salt such as palladium chloride, palladium acetate, palladium trifluoroacetate, and palladium acetylacetonate and an other transition metal salt such as nickel chloride and nickel acetate singly or preferably in combination with an oxidizing agent such as potassium permanganate, manganese dioxide, nickel peroxide, cupric sulfate, and silver oxide, in the presence or absence of an acid catalyst such as acetic acid, propionic acid, dichloroacetic acid, oxalic acid, succinic acid, glutaric acid, benzoic acid, 4-nitrobenzoic acid, 2,4-dinitrobenzoic acid, and toluenesulfonic acid and/or a quaternary ammonium salt such as benzyltriethylammonium chloride and tetrabutylammonium iodide. Any inert solvent can be used for the reaction. The reaction proceeds smoothly at 20–150° C.

Step 3

This step is a step to produce a compound shown by the formula (2a) or (2b) from a compound shown by the formula (4). The step can be performed according to well-known methods, for example, according to Bull. Chem. Soc. Jpn. 44, 474 (1971).

Step 4

This step is a step to produce a compound shown by the formula (3) by oxidative cyclization of a compound shown by the formula (2a) or (2b). The oxidative cyclization of this step is performed using a palladium salt such as palladium chloride, palladium acetate, palladium trifluoroacetate, and palladium acetylacetonate; an other transition metal salt such as nickel chloride and nickel acetate; and/or a heavy metal salt such as lead tetraacetate and cupric acetate singly or in a combination, in the presence or absence of a phosphine such as triphenylphosphine and trioctylphosphine; an organic base such as triethylamine, N-methylmorphine, and pyridine; an alkali metal salt such as sodium bicarbonate, potassium carbonate, sodium acetate, and potassium acetate; and/or a quaternary ammonium salt such as benzyltriethylammonium chloride and tetrabutylammonium iodide. Any inert solvent can be used for the reaction. The reaction proceeds smoothly at 20–150° C.

A compound shown by the formula (5), (6), or (7) can be derived from the compound shown by the formula (3) produced as above, according to the following steps 5–7, all of which can be performed, for example, according to J. Am. Chem. Soc. 114, 10056 (1992) and Japanese Patent Laid-open Pub. No. Hei 6-11629.

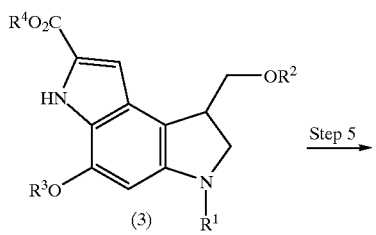

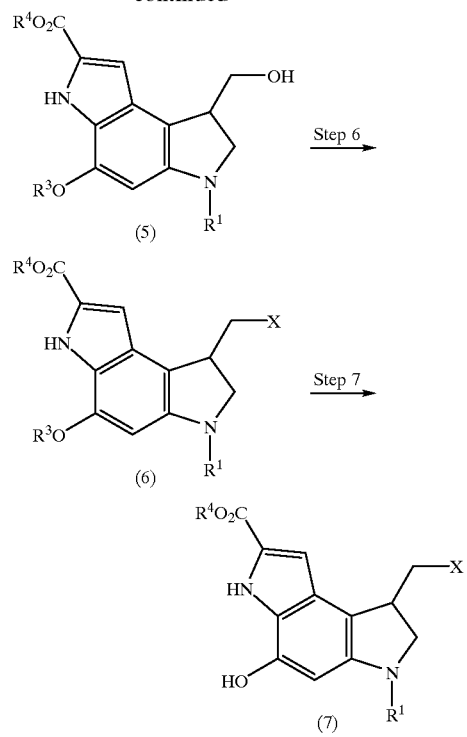

Wherein, $R^1$, $R^2$, $R^3$, and $R^4$ are the same as described above, X is a halogen.

BEST MODE FOR CARRYING OUT THE INVENTION

Examples are given below in order to show the usefulness of the present invention, but not to limit the scope of the present invention.

EXAMPLE 1

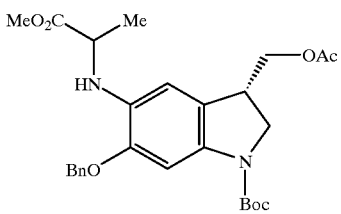

4.95 g (12.0 mmole) of 3S)-3-acetoxymethyl-5-amino-6-benzyloxy-1-t-butoxycarbonylindoline, 1.61 ml (14.4 mmole) of methyl 2-bromopropionate, and 3.09 g (14.4 mmole) of 1,8-bis(dimethylamino)naphthalene were heated to reflux in 18 ml of benzene at 90° C. for 50 hours. The reaction mixture was diluted with benzene, washed with water and saturated brine, dried over anhydrous sodium sulfate, and filtered, followed by condensation to give a residue. The residue was then purified by silica gel column chromatography with changing an eluate from hexane:ethyl acetate (4:1) to hexane:ethyl acetate (2:1) to give 5.82 g of (3S)-3-acetoxymethyl-5-[1-(methoxycarbonyl)ethyl]amino-6-benzyloxy-1-t-butoxycarbonylindoline. Yield, 97%. HRMS: 498.2366 calculated as $C_{27}H_{34}N_2O_7$; 498.2387 observed.

EXAMPLE 2

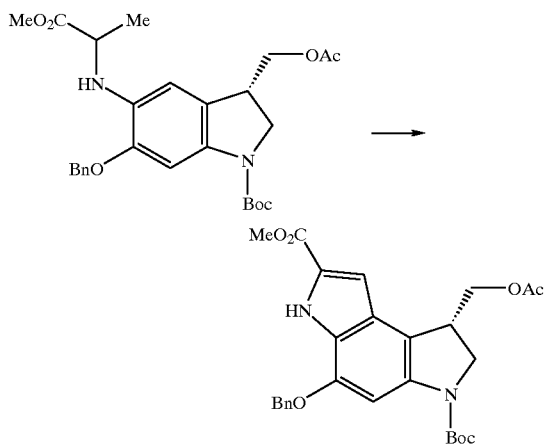

5.82 g (11.7 mmole) of (3S)-3-acetoxymethyl-5-[1-(methoxycarbonyl)ethyl]amino-6-benzyloxy-1-t-butoxycarbonylindoline, 5.24 g (23.4 mmole) of palladium acetate, 1.52 g (17.5 mmole) of manganese dioxide, and 1.95 g (11.7 mmole) of 4-nitrobenzoic acid were heated in 500 ml of dimethylacetamide at 90° C. for 18 hours. The reaction mixture was concentrated, ethyl acetate was added to the obtained residue, insoluble matter was removed by filtration, and the obtained filtrate was concentrated to give a residue. The residue was then purified by silica gel column chromatography with changing an eluate from benzene:ethyl acetate (5:1) to benzene:ethyl acetate (10:1) to give 1.34 g of methyl (1S)-1-acetoxymethyl-5-benzyloxy-3-t-butoxycarbonyl-1,2,3,6-tetrahydropyrrolo[3,2-e]indole-7-carboxylate. Yield, 23%. Mp. 128.5–129.5° C. (isopropyl ether). Elemental analysis: Calculated as $C_{27}H_{30}N_2O_7$: C,65.57; H,6.11; N,5.66 Found: C,65.40; H,6.05; N,5.64 NMR (CDCl$_3$) δ: 1.58 (9H, s), 2.10 (3H, s), 3.80–3.92 (2H, m), 3.92 (3H, s), 4.06 (1H, t, J=10.3 Hz), 4.15 (1H, dd, J=9.3, 11.2 Hz), 4.48 (1H, dd, J=5.4, 10.8 Hz), 5.22 (2H, s), 7.13 (1H, d, J=2.4 Hz), 7.39–7.48 (5H, m), 7.82 (1H, brs), 9.00 (1H, s). $[\alpha]_D^{25}=-11.1°$ (c 0.21, methanol).

EXAMPLE 3

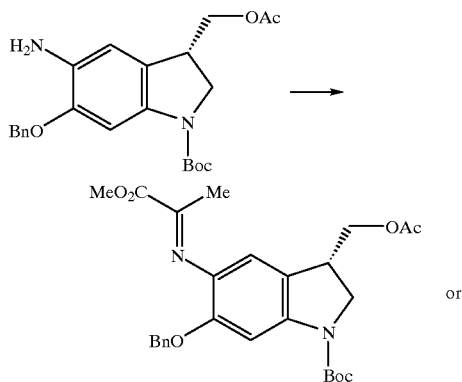

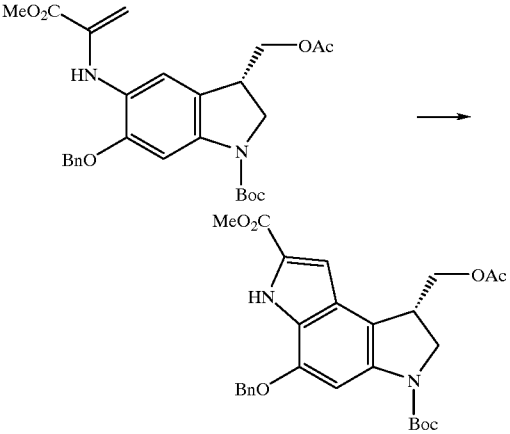

1.24 g (3.0 mmole) of (3S)-3-acetoxymethyl-5-amino-6-benzyloxy-1-t-butoxycarbonylindoline, 0.46 g (4.5 mmole) of methyl pyruvate, and 0.2 ml of acetic acid were heated to reflux in 30 ml of benzene for 5 hours using a Dean-Stark apparatus (Chem.Pharm.Bull. 24,1273 (1976)). The reaction mixture was washed with 5% sodium bicarbonate aqueous solution, dried over anhydrous sodium sulfate, and filtrated. The obtained filtrate was concentrated to give a residue, to which 1.35 g (6.0 mmole) of palladium acetate was then added, and the resulting mixture was heated in 100 ml of dimethylacetamide at 90° C. for 1 hour. The obtained reaction mixture was poured into water, the resulting mixture was thrice extracted with toluene-hexane (5:1), the combined organic layer was dried over anhydrous sodium sulfate, and filtrated. The obtained filtrate was concentrated to give a residue, which was then purified by silica gel column chromatography with changing an eluate from hexane:ethyl acetate (3:1) to hexane:ethyl acetate (2.5:1) to give 0.15 g of methyl (1S)-1-acetoxymethyl-5-benzyloxy-3-t-butoxycarbonyl-1,2,3,6-tetrahydropyrrolo[3,2-e]indole-7-carboxylate. Yield, 10%. This sample gave the same spectroscopic data as those obtained in Example 2.

REFERENCE EXAMPLE 1

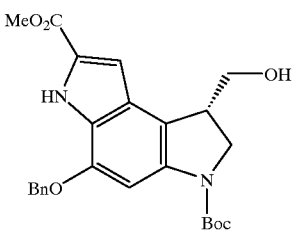

1.34 g (2.7 mmole) of methyl (1S)-1-acetoxymethyl-5-benzyloxy-3-t-butoxycarbony-1,2,3,6-tetrahydro[3,2-e]indole-7-carboxylate was suspended in 30 ml of methanol, 0.75 g (5.4 mmole) of potassium carbonate was added to the resulting suspension, followed by stirring at room temperature for 1 hour. The resulting reaction mixture was neutralized with 20% citric acid aqueous solution, and diluted with water, followed by extraction with ethyl acetate. The obtained organic layer was washed with saturated brine, dried over anhydrous sodium sulfate, and filtered. The obtained filtrate was concentrated to give a residue, which was then purified by silica gel column chromatography using an eluate of dichloromethane:ethyl acetate (5:1) to give 1.14 g of methyl (1S)-5-benzyloxy-3-t-butoxycarbonyl-1-hydroxymethyl-1,2,3,6-tetrahydropyrrolo[3,2-e]indole-7-carboxylate. Yield, 93%. NMR (CDCl$_3$) δ: 1.44 (1H, brs), 1.57 (9H, s), 3.74 (1H, m), 3.90 (2H, m), 3.92 (3H, s), 4.03 (1H, dd, J=3.9, 11.7 Hz), 4.16 (1H, t, J=10.8 Hz), 5.23 (2H, s), 7.12 (1H, s), 7.39–7.50 (5H, m), 7.84 (1H, brs), 9.01 (1H, s). [α]$_D^{25}$=−17.1° (c 0.20, methanol).

REFERENCE EXAMPLE 2

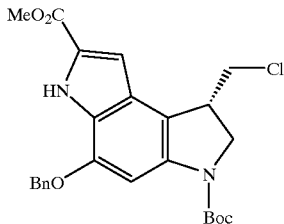

256.5 mg (0.57 mmole) of methyl (1S)-5-benzyloxy-3-t-butoxycarbonyl-1-hydroxymethyl-1,2,3,6-tetrahydropyrrolo[3,2-e]indole-7-carboxylate and 297.4. mg (1.13 mmole) of triphenylphosphine were dissolved in 6 ml of anhydrous dichloromethane, 0.33 ml (3.40 mmole) of carbon tetrachloride was added to the resulting solution, and the resulting mixture was stirred under argon atmosphere in the dark for 2 hours. The solvent was evaporated from the reaction mixture to give a residue, which was then purified by silica gel column chromatography using an eluate of hexane:ethyl acetate (4:1), followed by crystallization from hexane to give 245.3 mg of methyl (1S)-5-benzyloxy-3-t-butoxycarbonyl-1-chloromethyl-1,2,3,6-tetrahydropyrrolo[3,2-e]indole-7-carboxylate. Yield, 92%. NMR (CDCl$_3$) δ: 1.58 (9H, s), 3.56 (1H, t, J=9.8 Hz), 3.88–3.97 (2H, m), 3.93 (3H, s), 4.09 (1H, m), 4.19 (1H, m), 5.22 (2H, s), 7.08 (1H, d, J=2.0 Hz), 7.39–7.50 (5H, m), 7.81 (1H, brs), 9.03 (1H, s). [α]$_D^{25}$=−29.3° (c 0.18, methanol).

REFERENCE EXAMPLE 3

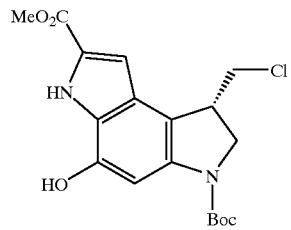

150.7 mg (0.32 mmole) of methyl (1S)-5-benzyloxy-3-t-butoxycarbonyl-1-chloromethyl-1,2,3,6-tetrahydropyrrolo[3,2-e]indole-7-carboxylate and 90 mg of 10% palladium carbon were suspended in 4 ml of tetrahydrofuran, and 1 ml of 25% ammonium formate aqueous solution was added dropwise under ice-cold condition, followed by stirring for 1 hour. The resulting reaction mixture was extracted with ethyl acetate, the obtained organic layer was dried over anhydrous sodium sulfate, and filtrated, followed by concentration to give a residue. The residue was then purified by silica gel column chromatography using an eluate of hexane:ethyl acetate (1:1), followed by crystallization with hexane to give 115.9 mg of methyl (1S)-3-t-butoxycarbonyl-1-chloromethyl-5-hydroxy-1,2,3,6-tetrahydropyrrolo[3,2-e]indole-7-carboxylate. Yield, 95%. NMR (CDCl$_3$) δ: 1.58 (9H, s), 3.54 (1H, t, J=9.8 Hz), 3.87–3.94 (2H, m), 3.96 (3H, s), 4.06 (1H, m), 4.17 (1H, dd, J=9.3, 11.7 Hz), 6.36 (1H, brs), 7.08 (1H, s), 7.64 (1H, brs), 9.23 (1H, brs). [α]$_D^{25}$=−42.6° (c 0.21, methanol).

INDUSTRIAL APPLICABILITY

A pyrroloindole derivative shown by the formula (3), which is an intermediate for a duocarmycin SA derivative which is expected to be used as an anticancer agent, can be easily produced by oxidative cyclization of an indole derivative shown by the formula(s) (1) and (2a) or (2b) which is produced according to the present invention. A pyrroloindole derivative shown by the formula (6) can be produced using a pyrroloindole derivative shown by the formula (3), and duocarmycin SA can be produced according to well-known methods. Optically active duocarmycin SA can be easily produced by using an optically active compound shown by the formula (4), for example, (3S)-3-acetoxymethyl-5-amino-6-benzyloxy-1-t-butoxycarbonylindoline (Japanese Patent Laid-open Pub. No. Hei 7-89933) according to the present invention.

What is claimed is:

1. An indole derivative shown by the formula (1),

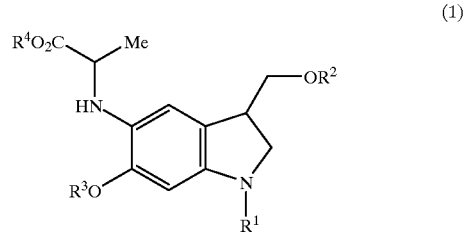

(1)

wherein R$^1$ is a t-butoxycarbonyl group; R$^2$ is a protecting group for hydroxyl group; R$^3$ is a protecting group for hydroxyl group; R$^4$ is a C$_1$–C$_6$ linear or branched lower alkyl group, or benzyl group.

2. An indole derivative shown by the formula (2a) or (2b),

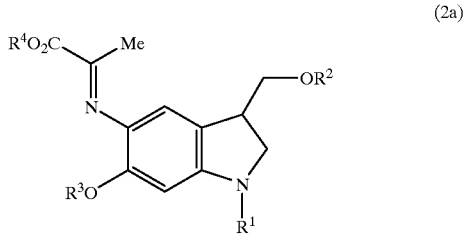

(2a)

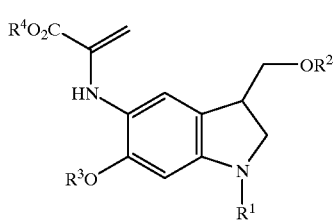

(2b)

wherein R$^1$ is a protecting group for amino group; R$^2$ is a protecting group for hydroxyl group; R$^3$ is a protecting group for hydroxyl group; R$^4$ is a C$_1$–C$_6$ linear or branched alkyl group, or benzyl group.

3. A pyrroloindole derivative shown by formula (3),

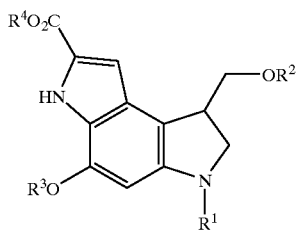
(3)

wherein $R^1$ is a protecting group for amino group; $R^2$ is an acetyl group; $R^3$ is a protecting group for hydroxyl group; $R^4$ is a $C_1$–$C_6$ linear or branched lower alkyl group, or benzyl group.

4. A method for producing a pyrroloindole derivative shown by the formula (3)

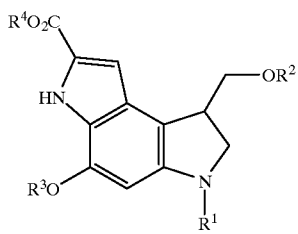
(3)

by oxidative cyclization of an indole derivative shown by the formula (1),

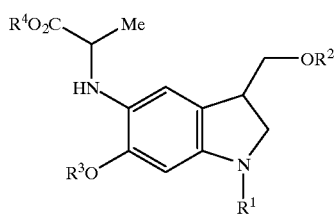
(1)

wherein $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group.

5. A method for producing a pyrroloindole derivative shown by the formula (3)

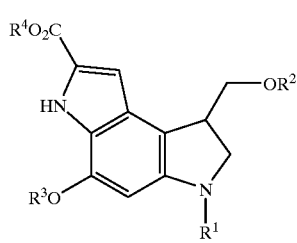
(3)

by oxidative cyclization of an indole derivative shown by the formula (2a) or (2b),

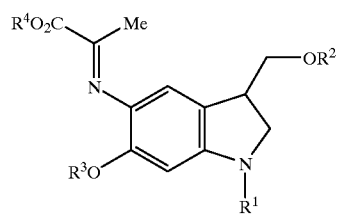
(2a)

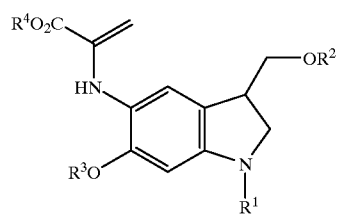
(2b)

wherein $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group.

* * * * *

(12) REEXAMINATION CERTIFICATE (4785th)
United States Patent
Fukuda et al.

(10) Number: US 6,066,742 C1
(45) Certificate Issued: May 20, 2003

(54) INTERMEDIATES FOR THE PREPARATION OF DUOCARMYCIN SA AND DERIVATIVES THEREOF, AND PROCESS FOR THE PRODUCTION OF THE INTERMEDIATES

(75) Inventors: Yasumichi Fukuda, Tochigi (JP); Shiro Terashima, Tokyo (JP)

(73) Assignees: Kyorin Pharmaceutical Co., Ltd., Tokyo (JP); Sagami Chemical Research Center, Sagamihara (JP)

Reexamination Request:
No. 90/006,164, Dec. 19, 2001

Reexamination Certificate for:
Patent No.: 6,066,742
Issued: May 23, 2000
Appl. No.: 09/254,515
Filed: Mar. 9, 1999

(22) PCT Filed: Jun. 26, 1997
(86) PCT No.: PCT/JP97/02207
§ 371 (c)(1),
(2), (4) Date: Mar. 9, 1999
(87) PCT Pub. No.: WO98/12197
PCT Pub. Date: Mar. 26, 1998

(30) Foreign Application Priority Data
Sep. 18, 1996 (JP) ............................................... 8-246097
(51) Int. Cl.[7] ...................... C07D 487/04; C07D 209/12
(52) U.S. Cl. ........................ 548/433; 548/491; 548/500
(58) Field of Search .................................. 548/491, 433

(56) References Cited

FOREIGN PATENT DOCUMENTS

WO WO 94/04534 3/1994

OTHER PUBLICATIONS

Jamart Gregoire et al., "Aggregative Activation and Heterocyclic Chemistry II Nucleophilic Condensations of Ketone Enolates on Dehydrodihydropyran Generated by Complex Bases," *Tetrahedron*, vol. 51, No. 7, pp. 1973–1984 (1995).
Quelet et al., "Sur La Synthese Des Indoles α–substitués," C.R. Hebd. Sciences Acad. Sci., vol. 249, pp. 1525–1528 (1959)(XP000983503).

*Primary Examiner*—Robert Gerstl

(57) ABSTRACT

Indole derivatives shown by the formulae (1), (2a) and (2b)

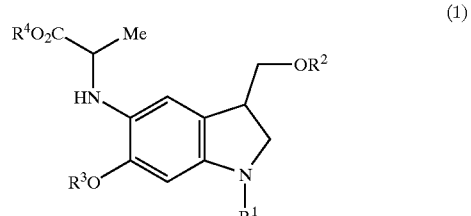

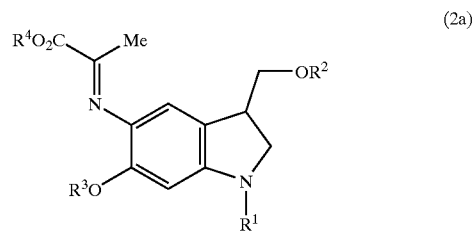

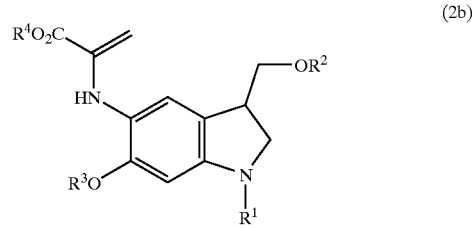

(wherein $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group), and pyrroloindole derivatives shown by formula (3)

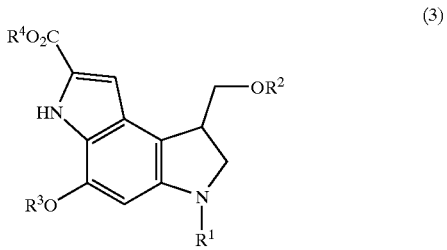

(wherein $R^1$ is a protecting group for amino group; $R^2$ is a protecting group for hydroxyl group; $R^3$ is a protecting group for hydroxyl group; $R^4$ is a $C_1$–$C_6$ linear or branched lower alkyl group, or benzyl group), both of which are intermediates for duocarmycin SA, which is expected to be used as an anticancer agent, and derivatives thereof; and a method for producing the same.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 is confirmed.

\* \* \* \* \*